United States Patent [19]

Tsuchihashi et al.

[11] 4,020,171

[45] Apr. 26, 1977

[54] CYCLIC KETONE MERCAPTAL S-OXIDES

[75] Inventors: Genichi Tsuchihashi, Tama; Katsuyuki Ogura, Sagamihara, both of Japan

[73] Assignee: Sagami Chemical Research Center, Japan

[22] Filed: Feb. 25, 1975

[21] Appl. No.: 552,737

[30] Foreign Application Priority Data

Mar. 4, 1974  Japan .............................. 49-24293
Mar. 4, 1974  Japan .............................. 49-24294

[52] U.S. Cl. .................. 260/340.5; 260/327 R; 260/327 TH; 260/329 R; 260/329 S; 260/332.3 R; 260/333; 260/345.1; 260/345.9; 260/347.2; 260/347.8; 260/456 NS; 260/338; 260/340.3; 260/607 A; 252/522

[51] Int. Cl.² ....................................... C07D 317/06
[58] Field of Search ................. 260/338, 340.5

[56] References Cited

UNITED STATES PATENTS 3,845,076  10/1974  Tsuchihashi et al. ....... 260/340.5 R

OTHER PUBLICATIONS

Ogura et al., Tetrahedron Letters, No. 10, pp. 759–762 (1976).
Ogura et al., Tetrahedron Letters, No. 41, pp. 3653–3656 (1974).
Herrmann et al., Tetrahedron Letters, (35) pp. 3271–3274 (1973).

Primary Examiner—James O. Thomas, Jr.
Assistant Examiner—G. T. Breitenstein
Attorney, Agent, or Firm—Wenderoth, Lind & Ponack

[57] ABSTRACT

Novel cyclic ketone mercaptal S-oxides and a process for preparing these compounds which comprises reacting formaldehyde mercaptal S-oxides with specific difunctional compounds.

4 Claims, No Drawings

CYCLIC KETONE MERCAPTAL S-OXIDES

This invention relates to novel cyclic ketone mercaptal S-oxides, and a process for preparing these compounds.

The novel cyclic ketone mercaptal S-oxides are expressed by the following formula

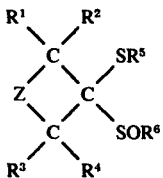

wherein $R^1$, $R^2$, $R^3$ and $R^4$, independently from each other, represent a hydrogen atom or an alkyl group containing 1 to 5 carbon atoms, $R^5$ and $R^6$ represent an alkyl group containing 1 to 5 carbon atoms, and Z represents an unsubstituted or substituted alkylene group containing 1 to 3 carbon atoms, an unsubstituted or substituted alkenylene group containing 2 to 3 carbon atoms, or a group resulting from the replacement of one —$CH_2$— group in the main chain of an unsubstituted or substituted alkylene group containing 1 to 3 carbon atoms by oxygen or sulfur.

When Z in formula (1) is a substituted alkylene group containing 1 to 3 carbon atoms, the preferred substituents are alkyl groups, such as those containing 1 to 5 carbon atoms, aralkyl groups such as a benzy group, alkoxy groups such as those containing 1 to 3 carbon atoms, and alkylidene dioxy groups such as those containing 1 to 3 carbon atoms. The alkenylene groups containing 2 to 3 carbon atoms represented by Z are

and

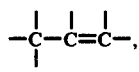

which can be substituted by suitable groups as in the case of the alkylene groups mentioned above. The group resulting from the replacement of one —$CH_2$— group in the main chain of the unsubstituted or substituted alkylene group containing 1 to 3 carbon atoms by oxygen or sulfur is, for example,

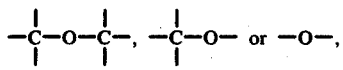

wherein O can be replaced by S.

The novel cyclic ketone mercaptal S-oxides of formula (1) in accordance with this invention are especially useful as precursors of the corresponding cyclic ketones or the acetals thereof. The compounds of formula (1) can be easily converted to the corresponding cyclic ketones by hydrolysis.

Generally, cyclic ketones occur in nature in the form of terpenes or steroids, and certain kinds of cyclic ketones are furnished by synthesis. These cyclic ketones have found a wide range of applications as, for example, physiologically active substances, and perfumes.

A number of methods have previously been known to synthesize cyclic ketones. A typical example comprises subjecting a diethyl ester of a 1, ω-alkanedicarboxylic acid to a Dieckmann reaction to form an α-ethoxycarbonyl cyclic ketone, and then hydrolyzing the product to decarboxylate it. This method, however, is commercially disadvantageous because decarboxylation results in the loss of one carbon atom. When a 4-membered cyclic ketone, a derivative of cyclobutanone, is to be prepared by the conventional method, the yield is extremely low, and therefore, the conventional process is limited to the synthesis of specific cyclic ketones. In contrast, by hydrolyzing the cyclic ketone mercaptal S-oxide in the presence of an acid, a cyclic ketone can be formed easily in a high yield, and various cyclic ketones corresponding to the starting materials can be obtained. This correspondingly to the starting materials. This will be described in detail hereinbelow.

According to this invention, the novel cyclic ketone mercaptal S-oxides of formula (1) can be easily prepared by the method to be disclosed.

This method comprises reacting difunctional compounds of the formula

wherein X and Y each represent a halogen atom, an alkanesulfonato group or an arene sufonato group, and $R^1$, $R^2$, $R^3$, $R^4$ and Z are the same as defined hereinabove, with formaldehyde mercaptal S-oxides of the formula

wherein $R^5$ and $R^6$ are the same as defined hereinabove, in the presence of a strong base.

Typical examples of X and Y in formula (2) are halogen atoms such as chlorine, bromine or iodine, alkanesulfonato groups such as methanesulfonato or ethanesulfonato, and arenesulfonator groups, for example, benzenesulfonato and substituted benzenesulfonato such as chlorobenzenesulfonato or toluenesulfonato.

Examples of preferred difunctional compounds of formula (2) include 1,ω-dihalo-substituted alkanes such as 1,3-dihalopropanes, 1,3-dihalo-2-benzylpropanes, 1,4-dihalobutanes, 1,4-dihalo-2,3-dialkoxybutanes, 1,4-dihalo-2,3-isopropylidenedioxybutanes or 1,5-dihalopentanes; dihalo ethers such as bis(2-chloroethyl)ether; dihalosulfides such as bis(2-chloroethyl) sulfide; 1,ω-dihaloalkenes such as cis-1,4-dichloro-2-butene; and compounds resulting from the replacement of the halogens in the above compounds by a sulfonato group. These compounds are readily available in the chemical industry.

The formaldehyde mercaptal S-oxides of formula (3) and the process for their preparation were invented by the same inventors as in the present application, and are disclosed in detail in U.S. Pat. No. 3,742,066 and West German Pat. No. 2,130,923.

Contacting the compounds of formula (2) with the compounds of formula (3) in the presence of a strong base readily yields the cyclic ketone mercaptal S-oxides of formula (1). Suitable strong bases include, for example, alkali metal hydrides such as LiH, NaH, or KH, alkali metal amides such as $NaNH_2$ or a lithium dialkylamide, alkyl alkali metals such as methyl lithium or butyl lithium, and aryl alkali metals such as phenyl lithium.

The reaction equivalents of the compound of formula (2) and the compound of formula (3) are stoichiometrically 1 mol of the compound (2) to 1 mol of the compound (3). The compound of formula (3) can, however, be used in excess, for example, up to about 2 mols. The amount of the strong base to be used is stoichiometrically 2 mols per mol of the compound of formula (2), but may be less, for example, 1 mol. The reaction would proceed smoothly even if the amount of the strong base is larger than 2 mols, but no special benefit can be obtained. If it is less than 1 mol, the yield of the desired product of formula (1) decreases.

Preferably, the reaction of forming the cyclic ketone mercaptal S-oxide of formula (1) is carried out in a solvent. Suitable solvents are aprotic solvents inert to the strong bases, for example, ethyl ether, dioxane, tetrahydrofuran, benzene, toluene, xylene, 1,2-dimethoxyethane, or hexamethylphosphoric triamide. Since the formaldehyde mercaptal S-oxide of formula (3) itself has a solvent action, the use of its in excess can obviate the use of another solvent in carrying out the reaction.

The reaction proceeds smoothly at a relatively low temperature, such as −80° C. to 100° C. Usually, reaction temperatures within the range 0° C. to 50° C. are applied. At these temperatures, the reaction time is usually about 1 hour to 30 hours. Isolation of the desired final product from the reacted mixture can be performed by conventional means such as extraction, chromatography, filtration or distillation.

As stated hereinabove, the cyclic ketone mercaptal S-oxides of formula (1) can be converted easily to the corresponding cyclic ketones of the formula

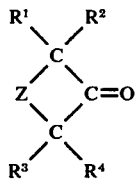

(4)

wherein $R^1$, $R^2$, $R^3$, $R^4$ and Z are the same as defined hereinabove,
by hydrolyzing the compounds of formula (1) in the presence of an acid catalyst. This reaction will be described in detail below.

The acid decomposition step is carried out by adding a catalytic amount of an acid or an aqueous solution of an acid to the cyclic ketone mercaptal S-oxides of formula (1) in the presence of a general solvent such as water, tetrahydrofuran, alcohols, acetonitrile, methylene chloride, chloroform or benzene. If desired, the amount of the acid can be increased. Examples of the acid include mineral acids such as sulfuric acid or hydrochloric acid, organic acids such as acetic acid, trifluoroacetic acid or paratoluenesulfonic acid, and Lewis acids such as copper chloride or trifluoroborane. The sulfuric acid and hydrochloric acid are preferred because of their low cost. Acetalizing agents such as ethyl ortho-formate can be added together with the acid. In this case, the cyclic ketones can be obtained in the form of ketals. The ketals assume the form of cyclic ketones whose carbonyl group is protected, and are regarded substantially as equivalent to the cyclic ketones themselves. The ketals can be easily converted to the corresponding cyclic ketones with dilute acids.

The acid decomposition step can proceed smoothly at a temperature in the vicinity of room temperature without requiring any particular heating or cooling means, but if desired, the reaction can be promoted by heating.

The cyclic ketone mercaptal S-oxide of formula (1) can be used either in the isolated form, or in the form of the reaction mixture containing the products formed by the reaction of the compound of formula (2) with the compound of formula (3). In either case, the desired cyclic ketone can be prepared in a high yield. After the reaction, the reaction mixture is neutralized with a basic substance such as sodium bicarbonate and extracted with ether. The ether layer is dried with anhydrous sodium sulfate, concentrated and then, for example, distilled to isolate the product in a pure form.

The following Examples A-1 to A-25 illustrate the preparation of the cyclic ketone mercaptal S-oxides of formula (1) by the reaction of the compounds of formula (2) with the compounds of formula (3), and Examples B-1 to B-17 illustrate the preparation cyclic ketones from the cyclic ketone mercaptal S-oxides.

EXAMPLE A-1

Potassium hydride (1.03g) was suspended in 15ml. of tetrahydrofuran, and with ice cooling, 1.398g of formaldehyde dimethyl mercaptal S-oxide was added. With ice cooling, the mixture was stirred for 40 minutes, and then 2.647 g (1.02 equivalents) of 1,5-dibromopentane was added gradually over the course of about 5 minutes. The mixture was stirred for 1 hour with ice cooling, and for 19 hours at room temperature. Then, 70 ml. of methylene chloride was added, and the insoluble matter which precipitated was separated by filtration. The filtrate was concentrated at reduced pressure, and separated by column chromatography (silica gel, eluted with $CH_2Cl_2$, 25% $AcOEt$-$CH_2Cl_2$, AcOEt, and MeOH) to afford 1.781g of cyclohexanone dimethyl mercaptal S-oxide as colorless crystals (recrystallized from benzene-n-hexane). The yield was 82%. The physical properties and the results of elemental analysis were as follows:
Melting point: 57.5°–58.5° C.
IR (KBr): 1045 $cm^{-1}$
NMR ($CDCl_3$): δ1.5–2.11m (10H), 2.08s(3H), 2.60s(3H)
For $C_8H_{16}OS_2$
Calculated: C, 49.95;H, 8.39;S, 33.34
Found: C, 50.18;H, 8.22;S, 33.26

EXAMPLE A-2

Formaldehyde dimethyl mercaptal S-oxide (1.44g) was dissolved in 15 ml. of tetrahydrofuran, and with ice cooling, 640 mg of sodium hydride was added, followed by stirring for 30 minutes. 1,5-Dibromopentane (3,160g) was added, and the mixture was stirred for 1 hour with ice cooling, for 24 hours at room temperature, and then for 8.5 hours at 50° C. Then, 70 ml. of methylene chloride was added, and the insoluble matter was separated by filtration. The filtrate was concentrated at reduced pressure. The residue was separated by column chromatography (silica gel, eluted with $CH_2Cl_2$) to afford 1.38 g of a light yellow oily substance. Analysis by NMR showed that it contained 943 mg of cyclohexanone dimethyl mercaptal S-oxide. The yield was 42%.

EXAMPLE A-3

Potassium hydride (995 mg) was suspended in 15 ml. dioxane, and with ice cooling, 1.804 g of formaldehyde diisopropyl mercaptal S-oxide was added gradually. The mixture was stirred for 1 hour with ice cooling, and then 2.411 g of 1,5-dibromopentane was added. Then, the mixture was stirred for 18 hours at room temperature. Methylene chloride (100ml) was added, and the isoluble matter was separated by filtration. After the evaporation of the filtrate at reduced pressure, the residue was separated by column chromatography (basic alumina, eluted with benzene, methylene chloride, and ethyl acetate) afford 1.463 g of cyclohexanone diisopropyl mercaptal S-oxide as a colorless oil. The yield was 59%. The physical properties and the results of elemental analysis were as follows:

IR (neat): 1050 cm$^{-1}$ NMR(CDCl$_3$): δ1.18d (3H, J=7HZ); 1.33d(6H, J=7Hz), 1.44d(3H, J=7Hz), 1.2–2.4m (10H), 3.16septet (1H, J=7Hz), 3.53septet(1H, J=7Hz)

For $C_{12}H_{24}OS_2$
Calculated: C, 58.01;H, 9.74:S, 25.81
Found: C, 57.87;H, 9.55;S, 25.72

EXAMPLE A-4

Potassium hydride (940 mg) was suspended in 15 ml. of tetrahydrofuran, and with ice cooling, 1.320g of formaldehyde dimethyl mercaptal S-oxide was added. With ice-cooling, the mixture was stirred for 40 minutes, and then 2.410 g of 1.4-dibromobutane was added. The mixture was stirred for 1 hour with ice cooling, and then for 19 hours at room temperature. Methylene chloride (70ml) was added, and the insoluble matter was separated by filtration. The filtrate was concentrated at reduced pressure, and the residue was separated by column chromatography (silica gel, eluted with $CH_2Cl_2$, 25% AcOEt-$CH_2Cl_2$, AcOEt, and MeOH) to afford 1.509 g of cyclopentanone dimethyl mercaptal S-oxide as a colorless oily substance. Furthermore, 208 mg of formaldehyde dimethyl mercaptal S-oxide was obtained from the MeOH fraction. The yield was 80%. The physical properties were as follows:

IR (neat) 1045 cm$^{-1}$
NMR(CDCl$_3$): δ1.6–2.3 m (3H), 2.18 s (3H), 2.64 s (3H)

The product was oxidized with hydrogen peroxide to convert it to its disulfone derivative, which was then subjected to elemental analysis.

Melting point: 173°–173.5° C.
IR(KBr): 1315, 1305, 1288, 1132, 550cm$^{-1}$
NMR(CDCl$_3$): δ1.7–2.2m (4H), 2.2–2.7m (4H) 3.17 s (6H)

For $C_7H_{14}O_4S_2$
Calculated: C, 37.15;H, 6.24;S, 28.34
Found: C, 37.29;H, 6.22;S, 28.31

EXAMPLE A-5

Formaldehyde dimethyl mercaptal S-oxide (1.49g) was dissolved in 15 ml. of tetrahydrofuran, and with ice cooling, 665 mg of sodium hydride was added. The mixture was stirred for 30 minutes with ice cooling, and then 2.936g of 1,4-dibromobutane was added. The mixture was stirred for 1 hour with ice cooling, for 24 hours at room temperature, and then for 44.5 hours at 50° C. Then, 100 ml. of methylene chloride was added, and the insoluble matter was separated. The filtrate was concentrated at reduced pressure, and the residue was separated by column chromatography (silica gel, eluted with 20% AcOEt-$CH_2Cl_2$, AcOEt, and MeOH) to afford 985 mg of cyclopentanone dimethyl mercaptal S-oxide. Also, 463 mg of formaldehyde dimethyl mercaptal S-oxide was recovered. The yield was 46%, and the conversion was 67%.

EXAMPLE A-6

Tetrahydrofuran (15 ml) was added to 1.01 g of potassium hydride, and with stirring under ice cooling, 1.004g of formaldehyde dimethyl mercaptal S-oxide was added dropwise. After stirring for 1 hour with ice cooling, 2.070g of 1,3-dibromopropane was added dropwise over the course of about 10 minutes. The mixture was stirred for 1 hour with ice cooling, and then for 17 hours at room temperature. Then, 100 ml. of methylene chloride was added, and the insoluble matter was separated by filtration. The filtration was concentrated at reduced pressure, and then separated by column chromatography (silica gel, eluted with methylene chloride, ether and methanol) to afford 1.081g of cyclobutanone dimethyl mercaptal S-oxide and 199 mg of formaldehyde dimethyl mercaptal S-oxide, both as a light yellow oil. The yield was 78%. The physical properties were as follows:

IR(neat): 1052 cm$^{-1}$
NMR(CDCl$_3$)- δ1.5–3.1 m (6H), 2.13 s (3H), 2.47 s(3H).

The S-oxide obtained was oxidized with hydrogen peroxide to form its disulfone derivative.

Melting point: 141.5 to 142° C.
IR (KBr): 1295, 1140, 1110, 945, 771, 505 cm$^{-1}$
NMR (CDCl$_3$): δ2.0–2.6m (2H), 2.7–3.1 m (4H), 3.15 L s (6H)

For $C_6H_{12}O_4S_2$
Calculated: C 33.94; H 5.70; S 30.21
Found: C 33.99; H 5.66; S 30.27

EXAMPLE A-7

Example A-6 was repeated except that 1.722 g of 1-bromo-3-chloropropane was used instead of 2.070 g of 1,3-dibromopropane. There was obtained 1.012 g of cyclobutanone dimethyl mercaptal S-oxide in a yield of 73%.

EXAMPLE A-8

Example A-6 was repeated except that 2.380 g of 1,3-bis(methanesulfonato)propane was used instead of 2.070g of 1,3-dibromopropane. There was obtained 739 mg of cyclobutanone dimethyl mercaptal S-oxide in a yield of 53%.

EXAMPLE A-9

Example A-6 was repeated except that 820 mg of butyl lithium and 1.400 of 1,3-dibromo-2-isobutylbutane were used respectively instead of 1.01g of potassium hydride and 2.070g of 1,3-dibromopropane. There was obtained 887 mg of 2-methyl-3-isobutyl cyclobutanone dimethyl mercaptal S-oxide in a yield of 45%.

EXAMPLE A-10

Potassium hydride (455 mg) was suspended in 10 ml. of tetrahydrofuran, and with stirring under ice cooling, 603 mg of formaldehyde dimethyl mercaptal S-oxide was added. The mixture was stirred for 1 hour with ice cooling, and then 1.115g of 2-benzyl-1,3-dibromopropane was added. The mixture was stirred for 1 hour with ice cooling, and then for 16 hours at room temperature. Then, 100 ml. of methylene chloride was added, and the insoluble matter was separated by filtration. The filtrate was concentrated at reduced pressure, and the residue was separated by column chromatography (silica gel, eluted with methylene chloride, ethyl acetate, and methanol) to afford 435 mg of a light yellow oily substance. Analysis by NMR showed that it contained 252 mg of 3-benzyl cyclobutanone dimethyl mercaptal S-oxide. The mixture was oxidized to form its disulfone derivative which was isolated. The physical properties and the result of elemental analysis were as follows:

Melting point: 125°–125.5° C. (recrystallized from methanol)
IR (KBr): 1315, 1300, 1130, 945, 745, 700, 520, 505 $cm^{-1}$
NMR($CDCl_3$): $\delta$2.6–3.0m (7H), 3.10s (3H) 3.17s (3H), 7.0–7.4 m(5H)
For $C_{13}H_{18}O_4S_2$
Calculated: C, 51.63; H, 6.00; S, 21.21
Found: C, 51.75; H, 6.03; S, 21.08

EXAMPLE A-11

Potassium hydride (910 mg) was suspended in 15 ml. of tetrahydrofuran, and with ice cooling, 1.301g of fomaldehyde dimethyl mercaptal S-oxide was added. The mixture was stirred for 30 minutes wit ice cooling, and then 2.950g of D,L-1,4-diiodo-2,3-dimethoxy butane was added. The mixture was stirred for 1 hour with ice cooling, and then for 15 hours at room temperature. Methylene chloride (100 ml) was added, and the insoluble matter was separated by filtration. The filtrate was concentrated at reduced pressure, and then separated by column chromatography (silica gel, eluted with ethyl acetate and methanol) to afford 1.998 g of 3,4-dimethoxycyclopentanone dimethyl mercaptal S-oxide in a yield of 80%.

EXAMPLE A-12

Example A-11 was repeated except that 3.085g of D,L-1,4-diido-2,3-isopropylidenedioxybutane was used instead of 2.95g of D,L-1,4-diiodo-2,3-dimethoxybutane. There was obtained 1.998g of 3,4-isopropylidenedioxycyclopentanone dimethyl mercaptal S-oxide in a yield of 76%.

EXAMPLE A-13

Potassium hydride (860 mg) was suspended in 15 ml. of tetrahydrofuran, and with ice cooling, 1.224 g of formaldehdye dimethyl mercaptal S-oxide was added. The mixture was stirred for 30 minutes with ice cooling, and then 1.513g of bis(2-chloroethyl) ether was added. The mixture was stirred for 1 hour with ice cooling, and then for 18 hours at room temperature. Methylene chloride (100 ml) was added, and the insoluble matter was separated by filtration. The filtrate was concentrated at reduced pressure, and separated by column chromatography (silica gel, eleuted with ethyl acetate and methanol) to afford 1.574 g of tetrahydro-α-pyrone dimethyl mercaptal S-oxide as a light yellow oily substance in a yield of 82%.

The physical properties were as follows:
IR(neat): 1048 $cm^{-1}$
NMR ($CDCl_3$): $\delta$1.4–1.8 m (2H), 2.2–2.6 m (2H), 2.13 s (3H), 2.61 s (3H), 3.8–4.1 m(4H)

The product was oxidized with hydrogen peroxide and $Na_2WO_4$ to form its disulfone derivative, which was then subjected to elemental analysis.
Melting point: 149°–149.5° C.
IR(KBr): 1315–1275, 1135, 1115–1095 $cm^{-1}$
NMR($CDCl_3$): $\delta$2.46t(4H, J=5.7Hz); 3.23s(6H), 4.04t(4H, J=5.7 Hz)
For $C_7H_{14}O_5S_2$
Calculated: C, 34.70; H, 5.82; S, 26.47
Found: C, 34.75; H, 5.86; S, 26.47

EXAMPLE A-14

Formaldehyde dimethyl mercaptal S-oxide (676 mg) was dissolved in 10 ml. of tetrahydrofuran, and 4.0 ml. of an n-hexane solution of n-butyl lithium (1.3 millimols/milliliter) was added at −70° C. The mixture was stirred for 1 hour at −70° C. to room temperature. After cooling the mixture to −70° C., 888 mg of L-1,4-diiode-2,3-isopropylidenedioxybutane was added. The mixture was stirred for 1 hour at −70° C. and then for 70 hours at room temperature. Then, 100 ml. of methylene chloride and 50 ml. of water were added, and the organic phase was separated. The aqueous phase was extracted twice with 20 ml. of methylene chloride each time, and with 20 ml. of ethyl acetate. The extract and the organic phase were combined, and dried with anhydrous sodium sulfate. The dried mixture was concentrated at reduced pressure, and the residue was separated by column chromatography (Florisil, eluted with ethyl acetate) to afford 381 mg of L-3,4-isopropylidenedioxycyclopentanone dimethyl mercaptal S-oxide in a yield of 66%. The physical properties were as follows:

IR(neat): 2987, 2995, 1373, 1383, 1151, 1120, 1050, 808, 769 $cm^{-1}$
NMR($CDCl_3$): $\delta$1.52 (S, 6H), 1.6–3.0 (m, 4H), 2.18 and 2.29 (S and S, total 3H), 2.57 and 2.63 (S and S, total 3H) 3,57–4.45 (m, 2H).

EXAMPLE A-15

Formaldehyde dimethyl mercaptal S-oxide (1.571 g) was dissolved in 15 ml. of tetrahydrofuran, and 8.9 ml. of an n-hexane solution of n-butyl lithium (1.4 millimols/milliliter) was added at −10° C. The mixture was stirred for 80 minutes, and then at −70° C., 1.125 g of 1,3-dibromobutane was added, and the mixture was stirred for 46.5 hours at room temperature. Methylene chloride (100 ml) was added. The mixture was washed with water and dried with anhydrous magnesium sulfate. It was concentrated at reduced pressure, and the residue was separated by column chromatography (Florisil, eluted with methylene chloride) to afford 746 mg of 2-methylcyclobutanone dimethyl mercaptal S- oxide. The product was oxidized with hydrogen peroxide and $Na_2WO_4$ to form its disulfone derivative.

The results of analysis were as follows:
Melting point: 99 to 102.5° C.
For $C_7H_{14}O_4S_2$
Calculated: C 37.15; H 6.24; S 28.33
Found: C 37.17; H 6.21; S 28.00

EXAMPLES A-16 to A-18

Formaldehyde dimethyl mercaptal S-oxide (designated A) was dissolved in 10 ml. of tetrahydrofuran, and at −10° C., an n-hexane solution (designated B; 1.4 millimols/milliliter) of n-butyl lithium was added. The mixture was stirred for 1 hour. After cooling the mixture to −70° C., a ;b 1ω-bis(p-toluenesulfonato)alkane (designated C) was added together with 10 ml. of tetrahydrofuran. The mixture was stirred for 18 hours at room temperature. Methylene chloride (100 ml) was added. The precipitate was washed with water, and dried with anhydrous magnesium sulfate. It was concentrated at reduced pressure, an separated by column chromatography (Florisil, eluted with methylene chloride) to afford a cycloalkanone dimethyl mercaptal S-oxide (designated D). The above reaction is schematically shown as follows:

$$CH_3SOCH_2SCH_3 + Tol \cdot SO_2O(CH_2)_nOSO_2Tol \cdot \xrightarrow{BuLi(B)}$$
$$(A) \qquad\qquad (C)$$

$$(CH_2)_n \quad C \begin{matrix} SCH_3 \\ \\ SOCH_3 \end{matrix}$$
$$(D)$$

The results are shown in Table 1 below together with the amounts of the compounds (A), (B) and (C).

| Example No. | n in (C) | (A) (g) | (B) (ml) | (C) (g) | (D) Yield (g) | Yield % |
|---|---|---|---|---|---|---|
| A-16 | 3 | 0.805 | 5.0 | 1.001 | 0.310 | 91 |
| A-17 | 4 | 1.690 | 9.6 | 2.245 | 0.837 | 84 |
| A-18 | 5 | 0.934 | 5.8 | 1.241 | 0.463 | 80 |

EXAMPLE A-19

Formaldehyde dimethyl mercaptal S-oxide (1.166g) was dissolved in 10 ml. of tetrahydrofuran, and at −16° C., 7.2 ml. of an n-hexane solution (1.4 millimols/milliliter) of n-butyl lithium was added, followed by stirring the mixture for 2.5 hours. 1,4-Bis(methanesulfonato)-butane (904 mg) was added together with 35 ml. of tetrahydrofuran. The mixture was stirred for 21 hours at room temperature. Then, the same procedure as in Example A-14 was repreated to afford 465 mg of cyclopentanone dimethyl mercaptal S-oxide in a yield of 71%.

EXAMPLE A-20

Formaldehyde dimethyl mercaptal S-oxide (880 mg) was dissolved in 20 ml. of tetrahydrofuran, and at −10° C. 5.30 ml of a n-hexane solution (1.3 millimols/milliliter) of butyl lithium was added. The mixture was stirred for 30 minutes at room temperature. At −68° C, 981 mg of L-(-)-2,3-dimethoxy-1,4-iodobutane was added, and the mixture was stirred for 1 hour at −68° C., and then for 29 hours at room temperature. Methylene chloride (100 ml) and 50 ml. of water were added, and the mixture was shaken. The organic phase was separated, and the aqueous phase was extracted thrice with 20 ml. of ethyl acetate each time. The extract and the organic phase were combined, and washed with a saturated aqueous solution of sodium chloride. The organic solution was dried with potassium carbonate and anhydrous sodium sulfate, and concentrated at reduced pressure. The residue was separated by column chromatograhy (Florisil, eluted with methylene chloride and ethyl acetate) to afford 457 mg of L-3,4-dimethoxycyclopentanone dimethyl mercaptal S-oxide as a light yellow oil in a yield of 72%.

The product was oxidized with hydrogen peroxide and $Na_2WO_4$ to form its disulfone derivative.

The physical properties and the results of elemental analysis were as follows:
Melting point: 93–93.5° C. (recrystallized from carbon tetrachloride)
NMR ($CDCl_3$): δ1.9–2.6 (m, 2H), 2.85 (m, 2H), 3.18 (s, 6H), 3.87 (m, 2H).
IR(KBr): 1312, 1139, 1122 $cm^{-1}$
For $CH_{18}O_6S_2$
Calculated: C, 37,82; H, 6.47
Found: C, 37.75; H, 6.34

EXAMPLE A-21

Formaldehyde dimethyl mercaptal S-oxide (959 mg) was dissolved in 10 ml. of tetrahydrofuran, and at −68° C., 5.9 ml. of a n-hexane solution (1,4 millimols/milliliter) of n-buttyl lithium was added. The mixture was stirred at room temperature for 1.5 hours, and cooled to −68° C. Meso-2,3-dimethoxy-1,4-iodobutane (1.143 g) was added. The mixture was stirred for 1 hour at −68° C., and then for 3 days at room temperature. Then, the procedure of Example A-20 was repeated to afford 466 mg of cis-3,4-dimethoxycyclopentanone dimethyl mercaptal S-oxide in a yield of 63%.

The physical properties were as follows:
NMR($CDl_3$): δ2.04 (m, 2H), 2.30 (S, 3H), 2.62(S, 3H) 2.5–3.0 (m, 2H), 3.40(S, 3H), 3,43 (S, 3H), 4.00 (m, 2H).
IR (neat): 1049 $cm^{-1}$ This product was oxidized with hydrogen peroxide and $Na_2WO_4$ to form its disulfone derivative.
Melting point: 175°–176° C.
For $C_9H_{18}O_6S_2$
Calculated: C 37.75; H 6.35; S 22.39
Found: C 37.98; H 6.30; S 22.36
MNR($CDCl_3$): δ2.57(m, 4H), 3.14(S, 3H) 3.21 (S, 3H), 3.40 (S, 6H), 3.98 (m, 2H)
IR(KBr): 1358, 1308, 1197, 1134, 1110, 1081, 1038, 1000, 974, 954, 834 $cm^{-1}$

EXAMPLE A-22

Formaldehyde dimethyl mercaptal S-oxide (1.010 g) was dissolved in 15 ml. of tetrahydrofuran, and at −10° C., 6.0 of an n-hexane solution (1.4 millimols/milliliter) of n-butyl lithium was added. The mixture was stirred at −10° C. for 1 hour, and then 1.030 g of 2-benzyl-1,3-dibromopropane was added. The mixture was stirred for 100 minutes at −10° C., and then for 3 hours at room temperature. Methylene chloride (100 ml) and 30 ml. of water were added and the inorganic phase was separated. The aqueous phase was extracted twice with 50 ml. of methylene chloride each time. The extract and the organic phase were combined, dried with anhydrous sodium sulfate, and concentrated at reduced pressure. The residue was separated by column chromatography (silica gel, eluted with methylene chloride and ethyl acetate) to afford 686 mg of 3-benzylcyclobutanone dimethyl mercaptal S-oxide as a light yellow oil in a yield of 77%.

The product was oxidized with hydrogen peroxide and Na$_2$WO$_4$ to form its disulfone derivative, and identified as the same product as obtained in Example A-10.

EXAMPLE A-23

Formaldehyde dimethyl mercaptal S-oxide (3.170g) was dissolved in 30 ml. of tetrahydrofuran, and at −15° C., 20 ml. of an n-hexane solution (1.3 millimols/milliliter) of n-butyl lithium was added. The mixture was stirred for 30 minutes at −15° C., and then 1.455g of cis-1,4-dichloro-2-butene was added. The mixture was stirred for 2.5 hours at −70° C. and then for 1.5 hours at room temperature. Methylene chloride (100 ml) and 30 ml. of water were added, and the mixture was shaken. The organic phase was separated, and the aqueous phase was extracted four times with 50 ml. of methylene chloride each time. The extract and the organic phase were combined, and dried with anhydrous sodium sulfate. The dried mixture was concentrated at reduced pressure, and the residue was separated by column chromatography (Florisil, eluted with methylene chloride and ethyl acetate) to afford 1.560 g of 3-cyclopentenone dimethyl mercaptal S-oxide and a light yellow oily substance in a yield of 76%.

The physical properties were as follows:
IR(neat): 1050 cm$^{-1}$
NMR(CDCl$_3$): δ2.24 (S, 3H), 2.60 (s,3H), 2.35–3.4 (m, 4H), 5.68 s (2H).

The product was oxidized with hydrogen peroxide and Na$_2$WO$_4$ to form its disulfone derivative.
Melting point: 168°–169° C. (recrystallised from acetone and carbon tetrachloride)
For C$_7$H$_{12}$O$_4$S$_2$
Calculated: C, 37.48; H, 5.39; S, 28.59
Found: C, 37.48; H, 5.38; S, 28.58.

EXAMPLE A-24

Potassium hydride (4.2g) was suspended in 50 ml. of tetrahydrofuran, and 5.464 g of formaldehyde dimethyl mercaptal S-oxide was added dropwise at −1020 C., The mixture was stirred for 1 hour at 0° C., and then a tetrahydrofuran solution (6.585 g/30 ml. ) of cis-1,4-dichloro-2-butene was added while adjusting the temperature of the reaction mixture to −30° to −40° C. Then, the mixture was stirred for 12.5 hours at room temperature. Methylene chloride (400 ml) and 50 ml. of water were added, and the mixture was shaken. The organic phase was separated, and the aqueous phase was extracted with methylene chloride. The extract and the organic phase were combined, dried with anhydrous sodium sulfate, and concentrated at reduced pressure. The residue was separated by column chromatography (Florisil, eluted with methylene chloride), to afford 3.461g of 3-cyclopentenone dimethyl mercaptal S-oxide in a yield of 45%.

EXAMPLE A-25

Formaldehyde dimethyl mercaptal S-oxide (1.27g) was dissolved in 15 ml. of tetrahydrofuran, and 246 mg of sodium hydride was added. The mixture was stirred for 30 minutes at room temperature, and then for 2 hours at 50° C. With ice cooling, 442 mg of cis-1,4-dichloro-2-butene was added. The mixture was stirred for 1 hour with ice cooling, and then for 6.5 hours at room temperature. Methylene chloride (100 ml) was added, and the insoluble matter was separated by filtration. The filtrate was concentrated at reduced pressure, and the residue was separated by column chromatography (Florisil, eluted with methylene chloride) to afford 382 mg of 3-cyclopentenone dimethyl mercaptal S-oxide in a yield of 61%.

EXAMPLE B-1

Cyclohexanone dimethyl mercaptal S-oxide (9.180g) was added to a mixture consisting of 14 ml. of ethanol, 12 ml. of ethyl ortho-formate and 0.2 ml. of conc. sulfuric acid, and the mixture was stirred for 14 hours at room temperature. Potassium carbonate (1.5g) was added at room temperature, and the mixture was stirred for 30 minutes. Further, 50 ml. of a 1N aqueous solution of potassium carbonate was added, and the reaction mixture was extracted thrice with 70 ml. of ether each time. The etheral phase was dried with potassium carbonate, and the ether was removed at atmospheric pressure. The residue was distilled at reduced pressure to afford 6.86g of a colorless liquid having a boiling point of 85° to 105° C. (mainly 100° to 105° C.)/157 mmHg. The product was identified as cyclohexanone diethyl acetal from its IR and NMR spectra.

EXAMPLE B-2

Ether (50 ml) was added to 10.790 g of cyclohexanone dimethyl mercaptal S-oxide (not completely dissolved). Dilute sulfuric acid (9N, 0.5 ml) was added, and the mixture was stirred for 3 hours at room temperature. Sodium bicarbonate (800 mg) was added, and the mixture was stirred for 30 minutes at room temperature. Anhydrous sodium sulfate (2.5g) was added to dry the mixture. The insoluble matter was separated by filtration, and the ether was removed at atmospheric pressure. The residue was distilled at reduced pressure to afford 4.327g of cyclohexanone in a yield of 79%.

EXAMPLEB-3

Ether (50 ml) was added to 10.14 g of cyclohexanone dimethyl mercaptal S-oxide, and 9.45 g of copper (II) chloride dihydrate was added. The mixture was stirred at room temperature for 20 hours, and heated under reflux for 5 hours. The insoluble matter was separated by filtration, and 50 ml. of water was added to the filtrate. The organic phase was separated. The aqueous phase was extracted three times with 70 ml. of ether each time. The extract and the organic phase were combined, dried with anhydrous sodium sulfate, and separated by distillation at reduced pressure and at atmopsheric pressure, thereby to afford 3.089 g of cyclohexanone in a yield of 60%.

EXAMPLE B-4

Cyclohexanone dimethyl mercaptal S-oxide (293mg) was dissolved in 3ml. of ethanol, and three drops of 9N dilute sulfuric acid were added. The mixture was stirred for 4 hours at room temperature. Analysis of the resulting product by thin-layer chromatography showed that no starting material remained. To the reaction mixture was added 14 ml. of solution containing 3g of 2,4-dinitrophenylhydrazine in 30 ml. of conc. sulfuric acid, 20 ml. of water, and 70 ml. of ethanol, and the mixture was allowed to stand overnight. Water (20 ml) was added, and 375 mg of the precipitated yellow crystals were isolated. The product was identified as a 2,4-dinitrophenylhydrazone derivative of cyclohexanone from its IR spectrum.

EXAMPLE B-5

Cyclohexanone diisopropyl mercaptal S-oxide (110 mg) was dissolved in 5 ml. of ethanol, and 0.2 ml. of acetic acid was added. The mixture was stirred at 60° C. for 5 hours, and the amount of the resulting cyclohexanone was determined by the reaction with 2,4-dinitrophenyl hydrazine. The yield was 75%.

EXAMPLE B-6

4-Phenycyclohexanone dimethy mercaptal S-oxide (350 mg) was dissolved in 5 ml. of ethanol, and two drops of 9N dilute sulfuric acid were added. The mixture was stirred for 5 hours at room temperature. The amount of the resulting 4-phenylcyclohexanone was determined by the reaction with 2,4-dinitrophenylhydrazine. The yield was 88%.

EXAMPLE B-7

Cyclopentanone dimethyl mercaptal S-oxide (211 mg) was dissolved in 5 ml. of ethanol, and five drops of 9N dilute sulfuric acid were added. The mixture was stirred for 15 hours at room temperature. Analysis of the product by thin-layer chromatography showed that no starting material remained. To the reaction mixture was added a solution containing 3g of 2,4-dinitorphenyl hydrazine in 30 ml. of conc. sulfuric acid, 20 ml. of water and 70 ml. of ethanol. The mixture was allowed to stand at room temperature for 4 hours, and then 20 ml. of water was added. Yellow crystals were precipitated in an amount of 290 mg. The product was identified as a 2,4-dinitrophenylhydrazone derivative of cyclopentanone from its IR spectrum. The yield was 92%.

EXAMPLE B-8

Example B-7 was repeated except that 281 mg of 2-methylcyclopentanone dimethyl mercaptal S-oxide was used instead of 211 mg of cyclopentanone dimethyl mercaptal S-oxide. There was obtained a 2,4-dinitrophenyl hydrazone derivative 2-methylcyclopentanone in a yield of 89%.

EXAMPLE B-9

Example B-7 was repeated except that 251 mg of 2,2-dimethylcyclopentanone dimethyl mercaptal X-oxide was used instead of 211 mg of cyclopentanone dimethyl mercaptal S-oxide. There was obtained a 2,4-dinitrophenyl hydrozone derivative of 2,2-dimethylcyclopentanone in a yield of 91%.

EXAMPLE B-10

Cyclobutanone dimethyl mercaptal S-oxide (432 mg) was dissolved in 3 ml. of ethanol, and 8 drops of 9N dilute sulfuric acid were added. The mixture was stirred for 18 hours at room temperature, and then for 5 hours at 45° C. Analysis of the product by thin layer chromatography led to the confirmation that there was no starting material remaining in the product. Then, 25 ml. of a solution containing 3 g of 2,4-dinitropnhenyl hydrazine in 30 ml. of sulfuric acid, 20 ml. of water, and 70 ml. of ethanol was added, and the mixture was allowed to stand overnight at room temperature. Water (20 ml) was added, and 518 mg of orange crystals having a melting point of 137° to 142° C. were obtained. Samples for analysis were obtained by recrystallizing the product from ethanol and carbon tetrachloride-n-hexane. The physical properties and the results of elemental analysis were as follows:

Orange crystals, m.p. 146.5°–148° C. (146° C., as found in literature)

IR(KBr): 3280, 3080, 1615, 1587, 1510, 1338, 1310, 1270 $cm^{-1}$

NMR($CDCl_3$) $\delta$1.9–2.5m (2H), 2.8–3.4m(4H), 7.87d(1H, J=10Hz), 8.27dxd (1H, J=2.5, 10Hz) 9.12d(1H, J=2.5Hz), 10.73 broad (1H, disappeared upon addition of $D_2O$).

For $C_{10}H_{10}N_4O_4$

Calculated: C, 48.00; H, 4.02; N, 22.39

Found: C, 47.97; H, 4.02; N, 22.17

*Literatue reference: N. J. Demjanov, M. Dogarenko, Chem. Ber., 55, 2739 (1932)

EXAMPLE B-11

Tetrahydro-γ-pyrone dimethyl mercaptal S-oxide (6.174g) was dissolved in 100 ml. of ether, and 1.0 ml. of 9N dilute sulfuric acid was added. The mixture was stirred at room temperature for 2 hours, and after adding 1.5 g of sodium bicarbonate, further stirred for 10 minutes. The reaction mixture was dried by the addition of anhydrous sodium sulfate, and the insoluble matter was separated by filtration. The ether was removed at atmospheric pressure. The residue was distilled at reduced pressure to afford 384 mg of a colorless liquid having a boiling point of 86 to 88° C./59 mmHg and 2.401 g of a colorless liquid having a boiling point of 88° to 91° C./59 mmHg. Analysis by NMR showed that the former was a mixture consisting of 92 mg of dimethyl disulfide and 292 mg of tetrahydro-γ-pyrone, and the latter, tetrahydro-γ-pyrone. The physical properties were as follows:

IR(neat): 1720, 1217, 1088, 990 $cm^{-1}$

NMR($CDCl_3$): $\delta$2.50 t(4H, J=6Hz), 3.98t(4H,J=6Hz)

The product was converted in a customary manner to its 2,4-dinitrophenyl hydrazone derivative.

Yellow crystals, m.p. 191.5–192.5° C. (186–187° C. as found in literature)

For $C_{11}H_{12}N_4O_5$

Calculated: C, 47.14; H, 4.32; N, 19.99

Found: C, 47.24; H, ;b 4.36; N, 19.74

Literature reference: M. I. Farberov, E. P. Tepenitsyna, and N. K. Shemyakina, Doklacly Akad. Nauk S.S.S.R., 99, 793 (1954); C.A., 49, 8315b (1955).

EXAMPLE B-12

Potassium hydride (10.51g) was suspended in 100 ml. of tetrahydrofuran, and with stirring under ice cooling, 14.01 g of formaldehyde dimthyl mercaptal S-oxide was added dropwise over the course of about 1 hour. With ice cooling, the mixture was stirred for 1 hour, and the, 27.70g of 1,5-dibromopentane was added dropwise over the course of about 1 hour. The mixture was stirred for 1 hour with ice cooling, and then for 15 hours at room temperature. Methylene chloride (200 ml) was added, and the insoluble matter was separated by filtration. The filtrate was concentrated at reduced pessure, and 30 L ml. of ethanol, 25 ml. of ethyl ortho-formate and 0.5 ml. of conc. sulfuric acid were added to the residue. The mixture was stirred for 15 hours at room temperature. Then, 3g of potassium carbonate was added, and the mixture was stirred at room temperature for 1 hour. An aqueous solution (1N, 100 ml) of potassium carbonate was added, and the mixture was extracted with ether. The extract was dried with potassium carbonate, and at atmospheric pressure, the ether was removed. The residue was distilled at reduced pressure to afford 13.52g of cyclohexanone diethyl acetal in a yield of 10%.

EXAMPLE B-13

Potassium hydride (3.92g) was suspended in 30 ml. of tetrahydrofuran, and with ice cooling, 4.984g of formaldehyde dimethyl mercaptal S-oxide was added dropwise for 40 minutes. With ice cooling, the mixture was stirred for 45 minutes, and then 5.822g of bis(2-chloroethyl) ether was added dropwise over the course of 30 minutes. The mixture was stirred for 1 hour with ice cooling, and then for 4 hours at room temperature. Methylene chloride (100 ml) was added, and the insoluble matter was separated by filtration. The filtrate was concentrated at reduced pressure, and the residue was dissolved in 100 ml. of ethyl ether, and 1.0 ml. of 4N hydrochloric acid was added. The mixture was stirred for 2 hours at room temperature, and 1.5 g of sodium bicarbonate was added, followed by stirring the mixture for 10 minutes. The mixture was dried with anhydrous sodium sulfate, and the insoluble matter was separated by filtration. The ethyl ether was removed at atmospheric pressure, and the residue was distilled at reduced pressure to afford 2.83 g of tetrahydro-$\gamma$-pyrone in a yield of 70%.

EXAMPLE B-14

Tetrahydrofuran (15 ml) was added to 1.00 g of potassium hydride, and with stirring under ice cooling, 1.034g of formaldehyde dimethyl mercaptal S-oxide was added dropwise. With ice cooling, the mixture was stirred for 1 hour, and then 2.114g of 1,3-dibromopropane was added dropwise over the course of about 10 minutes. The mixture was stirred for 1 hour with ice cooling, and then for 8 hours at room temperature. Methylene chloride (100 ml) was added, and the insoluble matter was separated by filtration. The filtrate was concentrated at reduced pressure, and the residue was dissolved in 10 ml. of ethanol. Dilute sulfuric acid (9N, 0.3 ml) was added, and the mixture was stirred for 5 hours at room temperature, and then for 5 hours at 50° C. The amount of the resulting cyclobutanone was determined by the reaction with 2,4-dinitrophenyl hydrazine. The yield was 64%.

EXAMPLE B-15

2-Methyl cyclobutanone dimethyl mercaptal S-oxide (212 mg) was dissolved in 3 ml. of ethanol, and 8 drops of 9N sulfuric acid were added. The mixture was stirred for 15 hours at room temperature, and then for 24 hours at 43° to 47° C. The resulting 2-methylcyclobutanone was converted to its 2,4-dinitrophenylhydrozone derivative in the same was as in Example 3-4. The amount of the 2,4-dinitrophenyl hydrazone obtained was 241 mg. The yield was 77%. The result of elemental analysis was as follows:

Melting point: 119.5° to 122° C. (recrystallized from ethanol-carbon tetrachloride)

For $C_{11}H_{12}N_4O_4$
Calculated: C, 50.00; H, 4.58; N, 21.20
Found: C, 50.07; H, 4.49; N, 20.99

EXAMPLE B-16

3Benzyl cyclobutanone dimethyl mercaptal S-oxide (398 mg) was dissolved in 20 ml. of ethyl ether, and 0.4 ml. of 9N dilute sulfuric acid was added. The mixture was stirred for 24 hours at room temperature, and then heated under reflux for 7 hours. The mixture was neutralized with sodium bicarbonate, and dried by the addition of anhydrous sodium sulfate. The insoluble matter was separated by filtration, and the filtrate was concentrated at reduced pressure. The residue (260 mg) identified as substantially pure 3-benzylcyclobutanone from its IR and NMR spectra.

IR (neat): 1785 cm$^{-1}$
NMR (CDCl$_3$): $\delta$2.43–3.49 (m, 7H), 7.21 (s, 5H)

The product was converted to its 2,4-dinitrophenyl hydrozone derivative in a customary manner, and subjected to quantitative and elemental analyses. The results were as follows:

Yield of 3-benzylcyclobutanone: 89%
Melting point of the 2,4-dinitrophenyl
hydrazone derivative: 138°–139.5° C (recrystallized from carbon tetrachloride-n-hexane)
For $C_{17}H_{16}N_4O_4$
Calculated: C 59.99; H 4.74; N 16.46
Found: C 60.02; H 4.70; N 16.46

EXAMPLE B-17

3-Cyclopentenone dimethyl mercaptal S-oxide (104 mg) was dissolved in 5 ml. of an 8:1 mixture of acetone and water, and 80 mg of copper (II) chloride and 50 mg of copper (II) oxide were added. The mixture was stirred for 5 hours at room temperature. Analysis of the product by gas chromatography (20%;XF 1150, N$_2$ 1 atm., 110° C.) showed that 26 mg of 3-cyclopentenone was formed. The yield was 53%.

What is claimed is:
1. A cyclic ketone mercaptal S-oxide of the formula

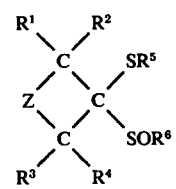

wherein R$^1$, R$^2$, R$^3$ and R$^4$, independently of each other, represent hydrogen or alkyl containing 1 to 5 carbon atoms, R$^5$ and R$^6$ represent alkyl containing 1 to 5 carbon atoms, and Z represents ethylene 1,2-substituted by isopropylidenedioxy.

2. A compound of claim 1 wherein R$^1$, R$^2$, R$^3$ and R$^4$ are hydrogen.

3. A compound of claim 1 wherein one of R$^1$, R$^2$, R$^3$ and R$^4$ is methyl.

4. A compound of claim 1 wherein R$^5$ and R$^6$ are methyl.

* * * * *